US010617531B2

(12) United States Patent
Guyer et al.

(10) Patent No.: US 10,617,531 B2
(45) Date of Patent: Apr. 14, 2020

(54) CERVICAL DISC AND INSTRUMENTATION

(71) Applicant: K2M, Inc., Leesburg, VA (US)

(72) Inventors: Rick Guyer, Dallas, TX (US); Patrick Melton, Vienna, VA (US); Nick Padovani, Arlington, VA (US); Josh Rubin, McLean, VA (US); Casey Lee, Florham Park, NJ (US)

(73) Assignee: K2M, Inc., Leesburg, VA (US)

( * ) Notice: Subject to any disclaimer, the term of this patent is extended or adjusted under 35 U.S.C. 154(b) by 152 days.

(21) Appl. No.: 15/332,105

(22) Filed: Oct. 24, 2016

(65) Prior Publication Data

US 2017/0112633 A1   Apr. 27, 2017

Related U.S. Application Data

(60) Provisional application No. 62/246,447, filed on Oct. 26, 2015.

(51) Int. Cl.
*A61F 2/44* (2006.01)
*A61F 2/46* (2006.01)
*A61F 2/30* (2006.01)

(52) U.S. Cl.
CPC ........ *A61F 2/4425* (2013.01); *A61F 2/30767* (2013.01); *A61F 2/4611* (2013.01); *A61F 2/4684* (2013.01); *A61F 2002/3013* (2013.01); *A61F 2002/30158* (2013.01); *A61F 2002/30492* (2013.01); *A61F 2002/30563* (2013.01); *A61F 2002/30884* (2013.01); *A61F 2002/443* (2013.01); *A61F 2002/4622* (2013.01); *A61F 2002/4623* (2013.01); *A61F 2002/4627* (2013.01); *A61F 2310/00407* (2013.01)

(58) Field of Classification Search
CPC ................................. A61F 2/44–447
See application file for complete search history.

(56) References Cited

U.S. PATENT DOCUMENTS 3,867,728 A   2/1975   Stubstad et al.
4,309,777 A   1/1982   Patil
(Continued)

FOREIGN PATENT DOCUMENTS

WO   2010034287 A2   4/2010

OTHER PUBLICATIONS

Extended European Search Report for European Application No. 16 19 5736 dated Mar. 17, 2017.
(Continued)

*Primary Examiner* — Nicholas J Plionis
(74) *Attorney, Agent, or Firm* — Lerner, David, Littenberg, Krumholz & Mentlik, LLP

(57) ABSTRACT

A spinal implant configured for positioning within a space between adjacent vertebral bodies includes an upper end plate including an outer surface extending between first and second end surfaces and opposed side surfaces. The outer surface includes a first convex profile extending between the first and second end surfaces and a second convex profile extending between the opposed side surfaces. The first convex profile and the second convex profile have different curvatures. The spinal implant further includes a lower end plate and a core disposed between the upper and lower end plates and coupled thereto. A method of assembling a spinal implant and a method of performing spinal surgery are also disclosed.

19 Claims, 11 Drawing Sheets

(56) References Cited

U.S. PATENT DOCUMENTS

| | | |
|---|---|---|
| 4,911,718 A | 3/1990 | Lee et al. |
| 4,932,969 A | 6/1990 | Frey et al. |
| 4,932,975 A | 6/1990 | Main et al. |
| 4,946,378 A | 8/1990 | Hirayama et al. |
| 4,997,432 A | 3/1991 | Keller |
| 5,002,576 A | 3/1991 | Fuhrmann et al. |
| 5,062,850 A | 11/1991 | MacMillan et al. |
| 5,071,437 A | 12/1991 | Steffee |
| 5,171,281 A | 12/1992 | Parsons et al. |
| 5,314,477 A | 5/1994 | Marnay |
| 5,314,478 A | 5/1994 | Oka et al. |
| 5,370,697 A | 12/1994 | Baumgartner |
| 5,401,269 A | 3/1995 | Buttner-Janz et al. |
| 5,458,642 A | 10/1995 | Beer et al. |
| 5,458,643 A | 10/1995 | Oka et al. |
| 5,534,029 A | 7/1996 | Shima |
| 5,534,030 A | 7/1996 | Navarro et al. |
| 5,545,229 A | 8/1996 | Parsons et al. |
| 5,556,431 A | 9/1996 | Buttner-Janz |
| 5,562,738 A | 10/1996 | Boyd et al. |
| 5,674,294 A | 10/1997 | Bainville et al. |
| 5,824,094 A | 10/1998 | Serhan et al. |
| 5,893,889 A | 4/1999 | Harrington |
| 6,139,579 A | 10/2000 | Steffee et al. |
| 6,162,252 A | 12/2000 | Kuras et al. |
| 6,348,071 B1 | 2/2002 | Steffee et al. |
| 6,368,350 B1 | 4/2002 | Erickson et al. |
| 6,369,350 B1 | 4/2002 | Norris |
| 6,395,032 B1 | 5/2002 | Gauchet |
| 6,402,785 B1 | 6/2002 | Zdeblick et al. |
| 6,419,706 B1 | 7/2002 | Graf |
| 6,527,804 B1 | 3/2003 | Gauchet et al. |
| 6,533,818 B1 | 3/2003 | Weber et al. |
| 6,562,624 B2 | 5/2003 | Adachi et al. |
| 6,579,320 B1 | 6/2003 | Gauchet et al. |
| 6,582,468 B1 | 6/2003 | Gauchet |
| 6,592,624 B1 | 7/2003 | Fraser et al. |
| 6,607,558 B2 | 8/2003 | Kuras |
| 6,626,943 B2 | 9/2003 | Eberlein et al. |
| 6,645,248 B2 | 11/2003 | Casutt |
| 6,669,732 B2 | 12/2003 | Serhan et al. |
| 6,682,562 B2 | 1/2004 | Viart et al. |
| 6,726,720 B2 | 4/2004 | Ross et al. |
| 6,733,532 B1 | 5/2004 | Gauchet et al. |
| 6,735,532 B2 | 5/2004 | Freed et al. |
| 6,749,635 B1 | 6/2004 | Bryan |
| 6,793,678 B2 | 9/2004 | Hawkins |
| 6,893,465 B2 | 5/2005 | Huang |
| 7,128,761 B2 | 10/2006 | Kuras et al. |
| 7,153,325 B2 | 12/2006 | Kim et al. |
| 7,156,848 B2 | 1/2007 | Ferree |
| 7,169,181 B2 | 1/2007 | Kuras |
| 7,250,060 B2 | 7/2007 | Trieu |
| 7,442,211 B2 | 10/2008 | de Villiers et al. |
| 7,585,325 B2 | 9/2009 | Schneid et al. |
| 7,731,753 B2 | 6/2010 | Reo et al. |
| 7,842,071 B2 * | 11/2010 | Hawkes ............ A61B 17/7052 606/252 |
| 7,850,697 B2 | 12/2010 | Ross et al. |
| 7,887,592 B2 | 2/2011 | Koske |
| 7,905,921 B2 | 3/2011 | Kim et al. |
| 8,038,715 B2 | 10/2011 | Kim et al. |
| 8,182,534 B2 * | 5/2012 | Ogilvie ................. A61F 2/442 623/17.15 |
| 8,277,508 B2 * | 10/2012 | Trieu ................... A61F 2/4425 623/17.15 |
| 8,377,138 B2 | 2/2013 | Reo et al. |
| 8,388,685 B2 | 3/2013 | Lombardo et al. |
| 8,403,987 B2 | 3/2013 | Reo et al. |
| 8,506,631 B2 | 8/2013 | de Villiers et al. |
| 8,518,116 B2 | 8/2013 | Lombardo et al. |
| 8,734,518 B2 | 5/2014 | Lombardo et al. |
| 8,808,381 B2 | 8/2014 | Kim et al. |
| 8,998,989 B2 | 4/2015 | Kim et al. |
| 9,044,278 B2 | 6/2015 | Tanaka |
| 9,084,688 B2 | 7/2015 | Hes et al. |
| 9,089,439 B2 | 7/2015 | Baumgartner et al. |
| 9,278,007 B2 | 3/2016 | Robinson |
| 9,566,167 B2 * | 2/2017 | Barrus ................. A61F 2/4465 |
| 2001/0016773 A1 | 8/2001 | Serhan et al. |
| 2001/0032017 A1 | 10/2001 | Alfaro et al. |
| 2002/0022888 A1 | 2/2002 | Serhan et al. |
| 2003/0045939 A1 | 3/2003 | Casutt |
| 2003/0074066 A1 | 4/2003 | Errico et al. |
| 2003/0100951 A1 | 5/2003 | Serhan et al. |
| 2003/0135277 A1 | 7/2003 | Bryan et al. |
| 2003/0187506 A1 * | 10/2003 | Ross ....................... A61F 2/442 623/17.13 |
| 2003/0208271 A1 | 11/2003 | Kuras |
| 2004/0054411 A1 | 3/2004 | Kelly et al. |
| 2004/0068320 A1 | 4/2004 | Robie et al. |
| 2004/0122517 A1 | 6/2004 | Kuras |
| 2004/0143332 A1 | 7/2004 | Krueger et al. |
| 2004/0193273 A1 | 9/2004 | Huang |
| 2004/0249462 A1 | 12/2004 | Huang |
| 2004/0267264 A1 * | 12/2004 | Konieczynski .... A61B 17/7032 606/289 |
| 2004/0267367 A1 | 12/2004 | O'Neil |
| 2005/0027300 A1 | 2/2005 | Hawkins et al. |
| 2005/0131544 A1 | 6/2005 | Kuras et al. |
| 2005/0192671 A1 | 9/2005 | Bao et al. |
| 2005/0197702 A1 | 9/2005 | Coppes et al. |
| 2005/0216081 A1 | 9/2005 | Taylor |
| 2005/0240267 A1 * | 10/2005 | Randall ................... A61F 2/44 623/17.11 |
| 2005/0261772 A1 * | 11/2005 | Filippi ................. A61F 2/4425 623/17.13 |
| 2005/0288788 A1 * | 12/2005 | Dougherty-Shah ........................ A61F 2/4465 623/17.11 |
| 2006/0025862 A1 * | 2/2006 | Villiers .................. A61F 2/4425 623/17.14 |
| 2006/0229724 A1 | 10/2006 | Lechmann et al. |
| 2006/0241760 A1 * | 10/2006 | Randall .................... A61F 2/447 623/17.11 |
| 2006/0265075 A1 | 11/2006 | Baumgartner et al. |
| 2006/0276900 A1 | 12/2006 | Carpenter |
| 2007/0055378 A1 * | 3/2007 | Ankney ............. A61B 17/1671 623/17.15 |
| 2007/0270958 A1 * | 11/2007 | Albans ................ A61F 2/30771 623/17.11 |
| 2009/0088853 A1 * | 4/2009 | Ogilvie .................... A61F 2/442 623/17.16 |
| 2009/0118836 A1 | 5/2009 | Cordaro |
| 2009/0326658 A1 * | 12/2009 | Allard ................... A61F 2/4425 623/17.16 |
| 2010/0070036 A1 | 3/2010 | Implicito |
| 2010/0274358 A1 | 10/2010 | Mueller et al. |
| 2011/0319996 A1 | 12/2011 | Barrall |
| 2012/0215314 A1 * | 8/2012 | Bennett ................. A61F 2/4425 623/17.16 |
| 2014/0094919 A1 * | 4/2014 | Mantri .................... A61F 2/442 623/17.16 |
| 2014/0277482 A1 | 9/2014 | Gfeller et al. |
| 2014/0316524 A1 | 10/2014 | Zimmers et al. |
| 2015/0039089 A1 | 2/2015 | Balasubramanian et al. |

OTHER PUBLICATIONS

International Search Report for Application No. PCT/US2017/029316 dated Aug. 24, 2017.

Spinel Kinetics, "Quality of Life, Quality of Motion", M6L Artificial Lumbar Disc product brochure, 2013, 6 pages.

Extended European Search Report including Written Opinion for Application No. EP17790236.8 dated Oct. 31, 2019.

* cited by examiner

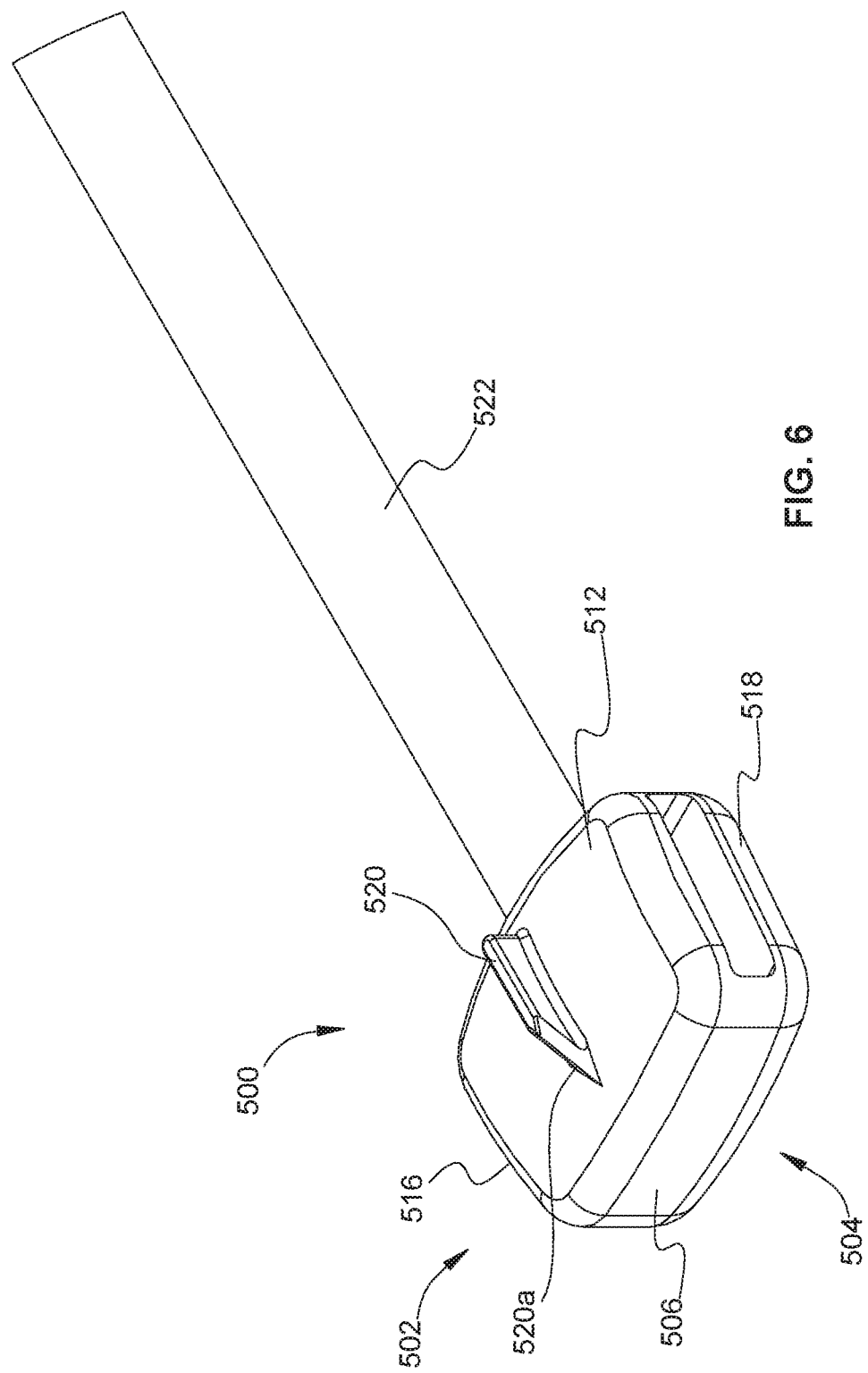

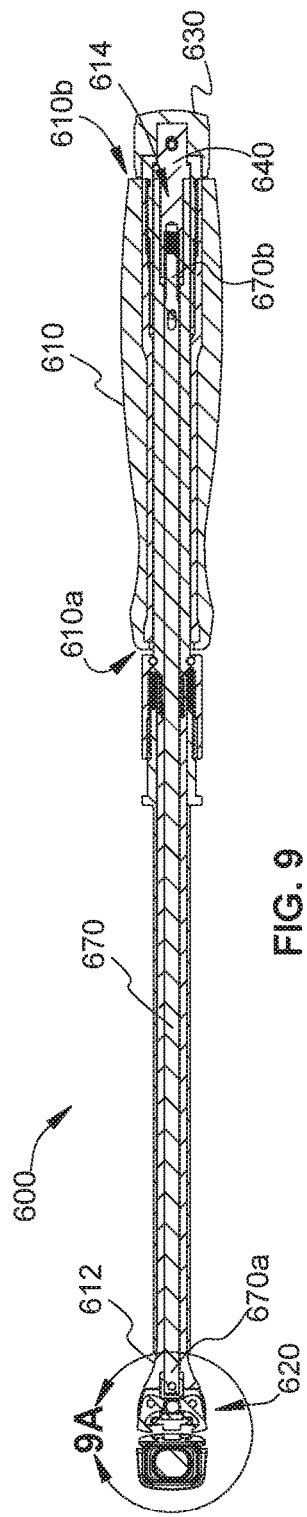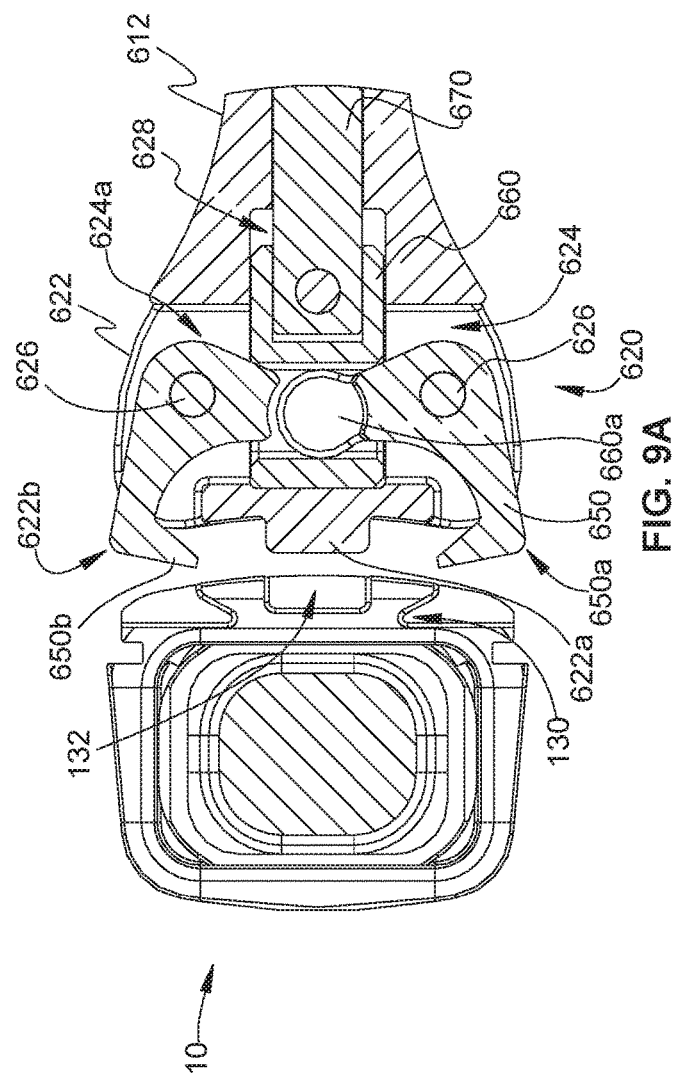

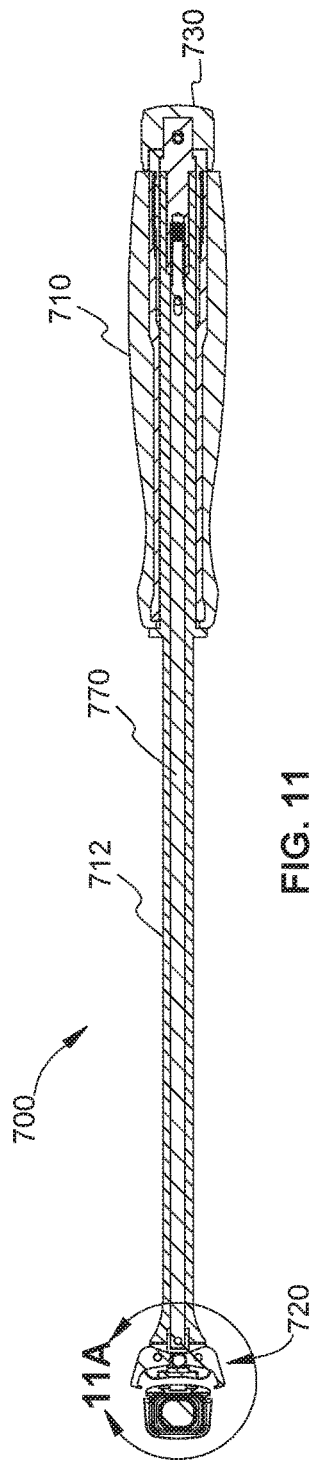
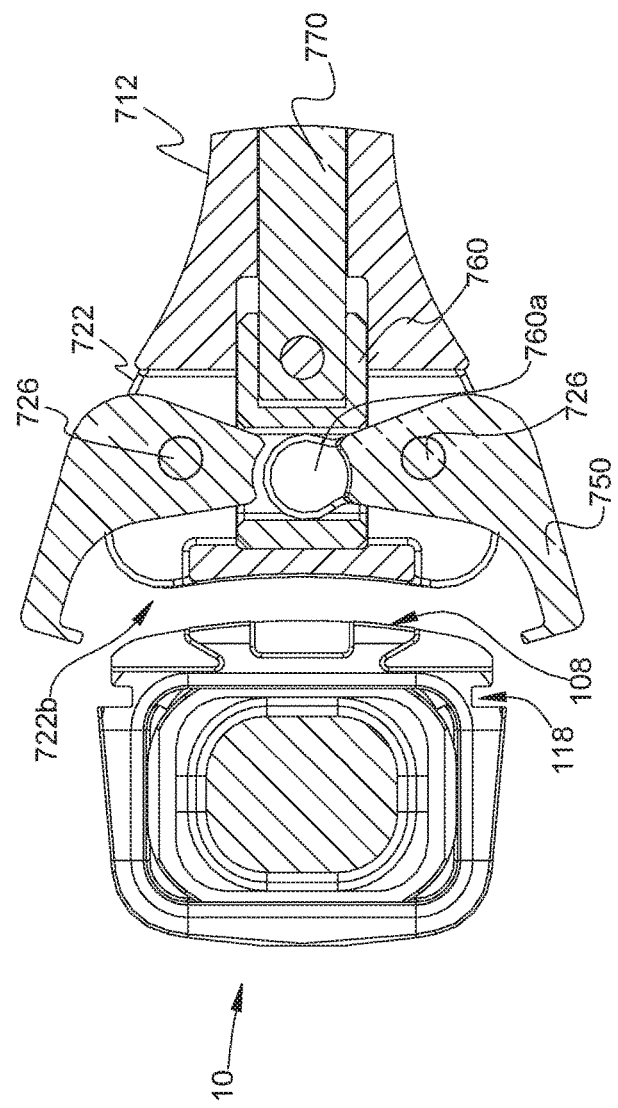
FIG. 11
FIG. 11A

CERVICAL DISC AND INSTRUMENTATION

CROSS-REFERENCE TO RELATED APPLICATIONS

This application claims priority to, and the benefit of, U.S. Provisional Patent Application Ser. No. 62/246,447, filed on Oct. 26, 2015, the entire content of which is hereby incorporated by reference herein.

TECHNICAL FIELD

The present disclosure relates generally to devices and methods for treating spinal conditions, and in particular, to spinal implants configured for positioning within an intervertebral space and associated instrumentation.

BACKGROUND

The human spine includes thirty-three vertebrae. The vertebrae interlock with one another to form a spinal column. Each vertebra has a cylindrical bony body (vertebral body), two pedicles extending from the vertebral body, a lamina extending from the pedicles, two wing-like projections extending from the pedicles, a spinous process extending from the lamina, a pars interarticularis, two superior facets extending from the pedicles, and two inferior facets extending from the lamina. The vertebrae are separated and cushioned by thin pads of tough, resilient fiber known as intervertebral discs. Intervertebral discs provide flexibility to the spine and act as shock absorbers during activity. A small opening (foramen) located between each vertebra allows passage of nerves. When the vertebrae are properly aligned, the nerves pass through without a problem. However, when the vertebrae are misaligned or a constriction is formed in the spinal canal, the nerves get compressed and may cause back pain, leg pain, or other neurological disorders.

Disorders of the spine that may cause misalignment of the vertebrae or constriction of the spinal canal include spinal injuries, infections, tumor formation, herniation of the intervertebral discs (i.e., slippage or protrusion), arthritic disorders, and scoliosis. In these pathologic circumstances, surgery may be tried to either decompress the neural elements and/or fuse adjacent vertebral segments. Decompression may involve laminectomy, discectomy, or corpectomy. Laminectomy involves the removal of part of the lamina, i.e., the bony roof of the spinal canal. Discectomy involves partial or complete removal of the intervertebral discs. Corpectomy involves removal of the vertebral body as well as the adjacent intervertebral discs.

The time-honored method of addressing the issues of neural irritation and instability resulting from severe disc damage have largely focused on removal of the damaged disc and fusing the adjacent vertebral elements together. Removal of the disc relieves the mechanical and chemical irritation of neural elements, while osseous union (bone knitting) solves the problem of instability.

While cancellous bone appears ideal to provide the biologic components necessary for osseous union to occur, it does not initially have the strength to resist the tremendous forces that may occur in the intervertebral disc space, nor does it have the capacity to adequately stabilize the spine until long term bony union occurs. For these reasons, many spinal surgeons have found that interbody fusion using bone alone has an unacceptably high rate of bone graft migration, expulsion, or nonunion due to structural failures of the bone or residual degrees of motion that retard or prohibit bony union. Therefore, intervertebral prostheses in various forms have been used to provide immediate stability and to protect and preserve an environment that fosters growth of grafted bone such that a structurally significant bony fusion can occur.

Due to a great deal of variation in the spinal columns of patients, implantation of intervertebral discs can be complex and can require a great deal of skill on the part of the surgeon. Therefore, a need exists for an intervertebral implant that enables easier implantation and effective performance after implantation within a large variety of patients.

SUMMARY

The present disclosure relates to spinal implants configured for positioning within an intervertebral space. The spinal implant includes an upper end plate including an outer surface extending between first and second end surfaces and opposed side surfaces. The outer surface includes a first convex profile extending between the first and second end surfaces and a second convex profile extending between the opposed side surfaces. The first convex profile and the second convex profile have different curvature. The spinal implant also includes a lower end plate and a core disposed between the upper and lower end plates and coupled thereto.

In aspects, the lower end plate may include an outer surface extending between first and second end surfaces and opposed side surfaces.

In some aspects, the spinal implant may further include a pair of antero-posterior fins disposed on each of the outer surfaces of the upper and lower end plates. The pairs of antero-posterior fins extend outwardly from the respective outer surfaces.

Each pair of antero-posterior fins may include an anterior fin and a posterior fin, wherein the anterior fin and posterior fin are spatially arranged such that a gap exists therebetween.

In embodiments, a leading edge of each posterior fin may be chamfered such that the height of the posterior fin increases in an anterior direction.

In aspects, each of the upper and lower end plates may include a trapezoidal profile in a plan view.

In some aspects, the perimeter of each of the outer surfaces of the upper and lower end plates may be rounded. The rounded perimeter includes a radius that is less than that of the outer surfaces of the upper and lower end plates.

In aspects, the outer surfaces may include a titanium spray coating.

A proximal end of each of the upper and lower end plates may include a pair of reliefs configured to releasably engage an insertion tool.

In embodiments, a proximal end of each of the upper and lower end plates may further include a pair of notches configured to releasably engage a removal tool.

According to yet another aspect, the present disclosure is directed to a method of assembling a spinal implant. The method includes providing an upper end plate and a lower end plate, each including an outer surface extending between first and second end surfaces and opposed side surfaces. The outer surface of each of the upper and lower end plates includes a first convex profile extending between the first and second end surfaces and a second convex profile extending between the opposed side surfaces. The first convex profile and the second convex profile have different curvatures. The upper and lower end plates further include a respective inner surface extending between the first and second end surfaces and opposed side surfaces and the inner surfaces include a coupling recess defined therein. The method further includes providing a core configured to releasably engage a retaining groove defined in a peripheral sidewall of each respective coupling recess, advancing the core within the coupling recess of the upper end plate, sliding the core in a distal direction to engage the retaining groove of the upper end plate, advancing a first retaining rod within a first lumen defined through one of the opposed side surfaces of the upper end plate, deforming the first retaining rod to secure the core within the coupling recess of the upper end plate, advancing an opposite end of the core within the coupling recess of the lower end plate, sliding the core in a distal direction to engage the retaining groove of the lower end plate, advancing a second retaining rod within a second lumen defined through one of the opposed side surfaces of the lower end plate, and deforming the second retaining rod to secure the core within the coupling recess of the lower end plate.

The method may include inserting a tool within a throughbore defined through respective outer surfaces of upper and lower end plates to deform each of the first and second retaining rods.

A method of performing spinal surgery is provided according to another aspect of the present disclosure. The method includes providing a spinal implant including an upper end plate including an outer surface extending between first and second end surfaces and opposed side surfaces. The outer surface includes a first convex profile extending between the first and second end surfaces and a second convex profile extending between the opposed side surfaces. The first convex profile and the second convex profile have different curvatures. The spinal implant further includes a lower end plate and a core disposed between each of the upper and lower end plates and coupled thereto. The method further includes preparing an intervertebral space between first and second vertebral bodies to receive the spinal implant and inserting the spinal implant into the prepared intervertebral space.

In embodiments, preparing an intervertebral space may further include inserting a trial inserter within the intervertebral space to cut a groove in each of the first and second vertebral bodies.

In aspects, inserting the spinal implant into the prepared intervertebral space may further include aligning anteroposterior fins disposed on outer surfaces of the upper and lower end plates with the groove cut in the first and second vertebral bodies.

In some aspects, the method includes selectively engaging an insertion tool to a proximal end of the spinal implant.

In aspects, selectively engaging an insertion tool includes rotating an actuation knob disposed on a proximal end thereof the rotate a pair of opposed jaw members disposed on a distal end of the insertion tool from a first, open position, to a second approximated position.

The method may further include selectively engaging a removal tool to a proximal end of the spinal implant.

In embodiments, selectively engaging a removal tool may include rotating an actuation knob a proximal end thereof the rotate a pair of opposed jaw members disposed on a distal end of the insertion tool from a first, open position, to a second approximated position.

In aspects, the method may further include pulling the removal tool in a proximal position to remove the spinal implant from the intervertebral space.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiments given below, serve to explain the principles of the disclosure, wherein:

FIG. 6 is a top, perspective, view of a trial inserter provided in accordance with the present disclosure;

FIG. 9 is top, cross-sectional, view of an insertion tool provided in accordance with the present disclosure, shown in an open position;

FIG. 9A is an enlarged view of the area of detail of FIG. 9;

FIG. 11 is a top, cross-sectional, view of a removal tool provided in accordance with the present disclosure, shown in an open position;

FIG. 11A is an enlarged view of the area of detail of FIG. 11;

DETAILED DESCRIPTION

Figure 1:
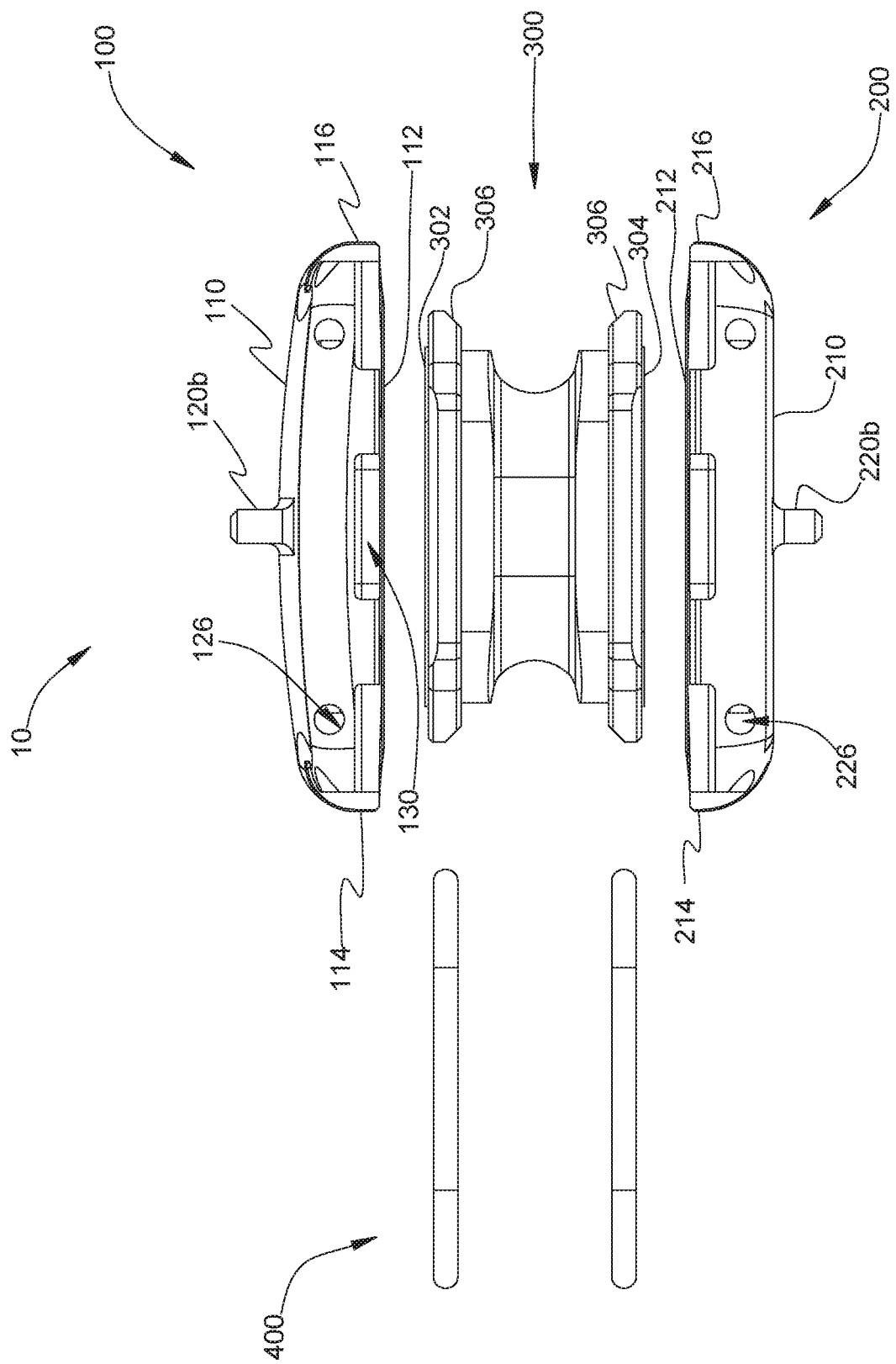
FIG. 1 is a front view of a spinal implant provided in accordance with the present disclosure, with parts separated.

Embodiments of the present disclosure are now described in detail with reference to the drawings in which like reference numerals designate identical or corresponding elements in each of the several views. As commonly known, the term "clinician" refers to a doctor, a nurse or any other care provider and may include support personnel. Additionally, the term "proximal" refers to the portion of the device or component thereof that is closer to the clinician and the term "distal" refers to the portion of the device or component thereof that is farther from the clinician. In addition, the term "cephalad" is used in this application to indicate a direction toward a patient's head, whereas the term "caudal" indicates a direction toward the patient's feet. Further still, for the purposes of this application, the term "lateral" indicates a direction toward a side of the body of the patient, i.e., away from the middle of the body of the patient. The term "medial" indicates a direction toward the midline of the patient, i.e., toward the middle of the body of the patient. The term "posterior" indicates a direction toward the patient's back, and the term "anterior" indicates a direction toward the patient's front. Additionally, in the drawings and in the description that follows, terms such as front, rear, upper, lower, top, bottom, and similar directional terms are used simply for convenience of description and are not intended to limit the disclosure. In the following description, well-known functions or constructions are not described in detail to avoid obscuring the present disclosure in unnecessary detail.

Referring now to the drawings, FIGS. 1-5A illustrate one embodiment of a spinal implant provided in accordance with the present disclosure and generally identified by reference numeral 10. Spinal implant 10 generally includes upper and lower end plates 100 and 200, core 300, and retaining pins 400. Each of these components along with the assembly and insertion of spinal implant 10 into the intervertebral space between adjacent vertebral bodies will be described in turn hereinbelow.

Figure 2:
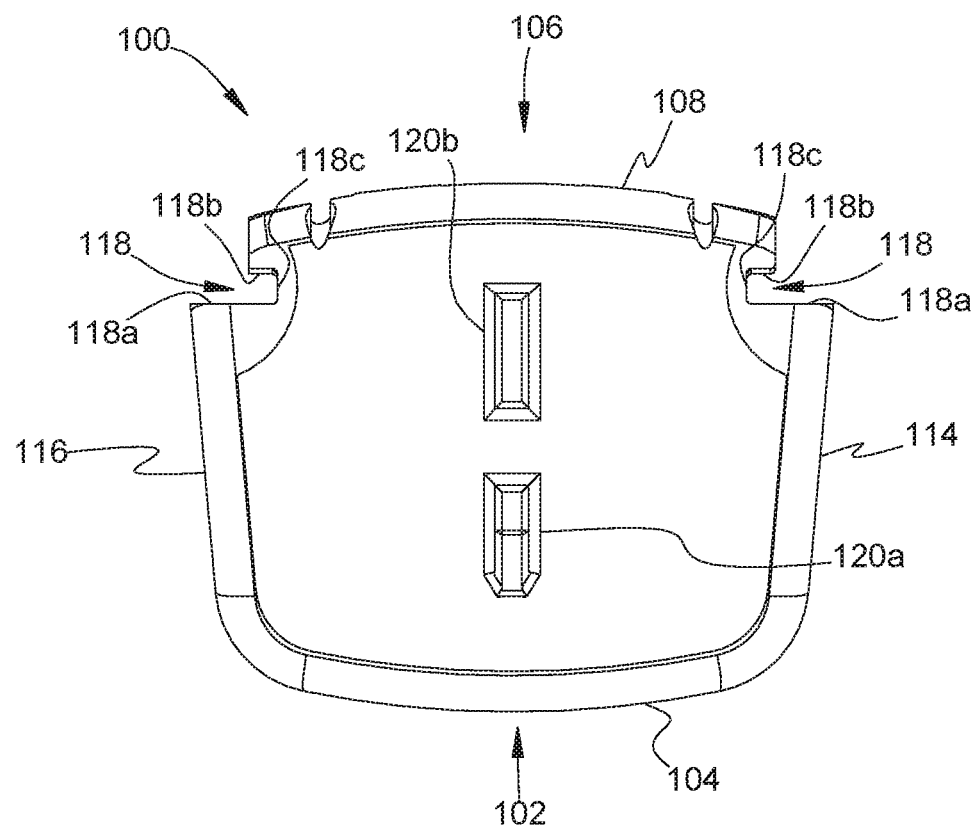
FIG. 2 is a top view of the spinal implant of FIG. 1.

Upper end plate 100 is illustrated as having a generally trapezoidal shaped profile (FIG. 2), although other suitable shapes are contemplated, such as square, rectangular, circular, oval, or the like. As best illustrated in FIG. 2, upper end plate 100 includes an arcuate, first end surface 104, at a distal or leading end 102, and a second end surface 108, opposite thereto at a proximal or trailing end 106, having an arcuate configuration. In embodiments, first and second end surfaces 104, 108 may include a substantially planar configuration. Upper end plate 100 extends between first and second end surfaces 104, 108 to define respective outer and inner surfaces 110 and 112 (FIG. 3), respectively, as well as opposed side surfaces 114 and 116 (FIG. 2). Opposed side surfaces 114, 116 are generally shown as forming a diverging angle with respect to first end surface 104, although it is contemplated that opposed side surfaces 114, 116 may extend perpendicularly from first end surface 104 parallel to each other or form a converging angle with respect thereto.

Figure 12:
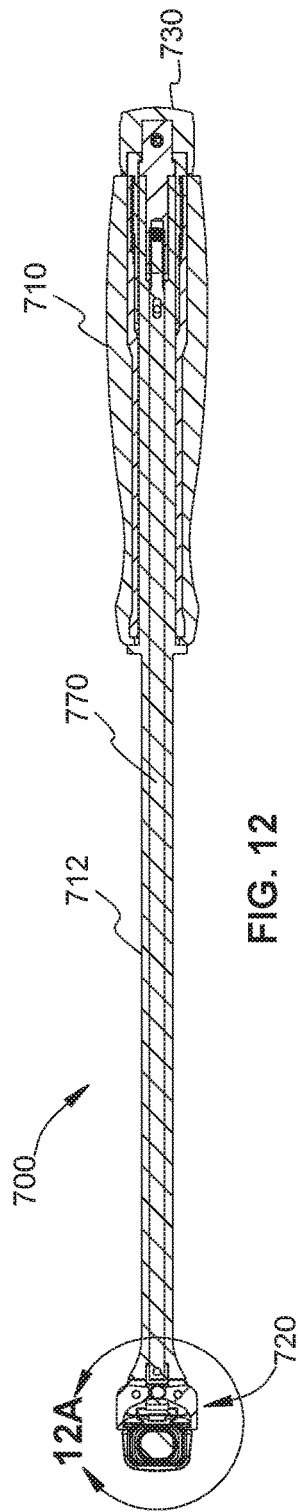
FIG. 12 is a top, cross-sectional view of the removal tool shown in an approximated position.

With reference to FIG. 2, upper end plate 100 includes a pair of opposed notches 118 defined through outer and inner surfaces 110, 112 at a location adjacent second end surface 108. Notches 118 define distal and proximal end surfaces 118a and 118b and inner surface 118c. In this manner, second end surface 108 is truncated as it extends outward from an interior portion of upper end plate 100, i.e., second end surface 108 does not extend to opposed side surfaces 114, 116. As will be described in more detail below, this configuration facilitates selective engagement with a suitable removal tool, such as removal tool 700 (FIGS. 11 and 12).

Figure 3:
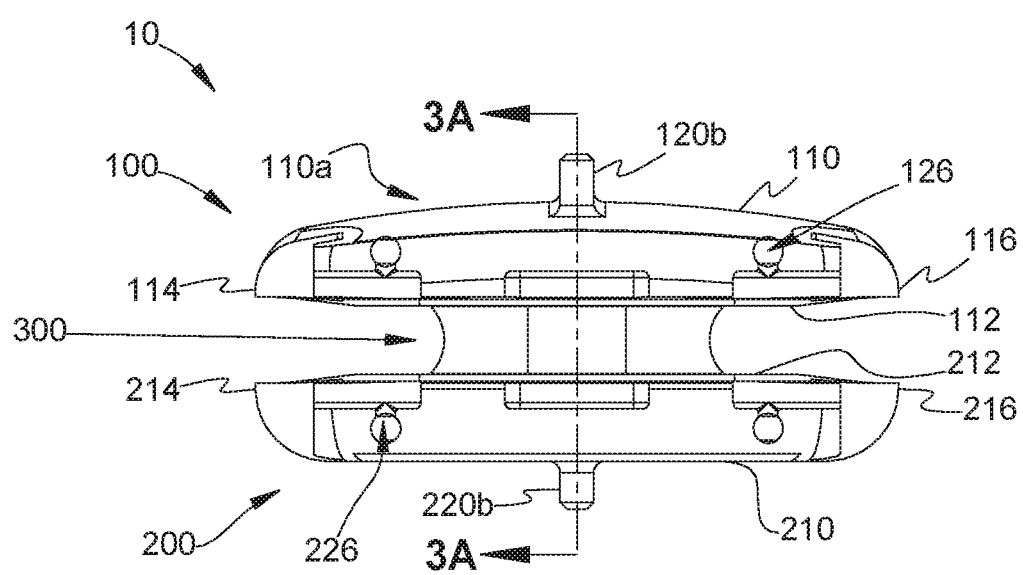
FIG. 3 is a front view of the spinal implant of FIG. 1.

Referring now to FIG. 3, outer surface 110 of upper end plate 100 includes a first convex profile 110a extending between opposed side surfaces 114, 116, although other suitable profiles are also contemplated. The perimeter of outer surface 110 may be rounded to enhance the atraumatic character of upper end plate 100. In this manner, the radius of the perimeter of outer surface 110 may be smaller than that of outer surface 110 (i.e., the radius of outer surface 110 decreases in a direction towards its perimeter, thereby increasing the blunt nature of the perimeter of outer surface 110). It is contemplated that the radius of the perimeter of outer surface 110 may be between 0.25 inches and 0.75 inches. In embodiments, the radius of first convex profile 110a is 1.5 inches, although other suitable dimensions are also contemplated, such as a radius between 1.3 inches and 1.7 inches.

Upper end plate 100 includes a plurality of anteroposterior fins 120a and 120b (FIG. 2) extending vertically from outer surface 110 to enhance fixation of the upper end plate 100 to a vertebral endplate and to provide additional support during torsional loading. Fins 120a, 120b are disposed centrally on outer surface 110 and are spatially arranged such that a gap exists between each of fins 120a, 120b in an antero-posterior direction. In embodiments, spinal implant 10 is inserted within the intervertebral space between vertebral bodies from an anterior approach. Thus, fin 120a may be referred to as an anterior fin and fin 120b may be referred to as a posterior fin. A leading edge (FIGS. 3A and 4) of fin 120a is chamfered such that the height of fin 120a increases in an anterior or proximal direction to facilitate smoother insertion of upper end plate 100 within the intervertebral space.

Figure 4:
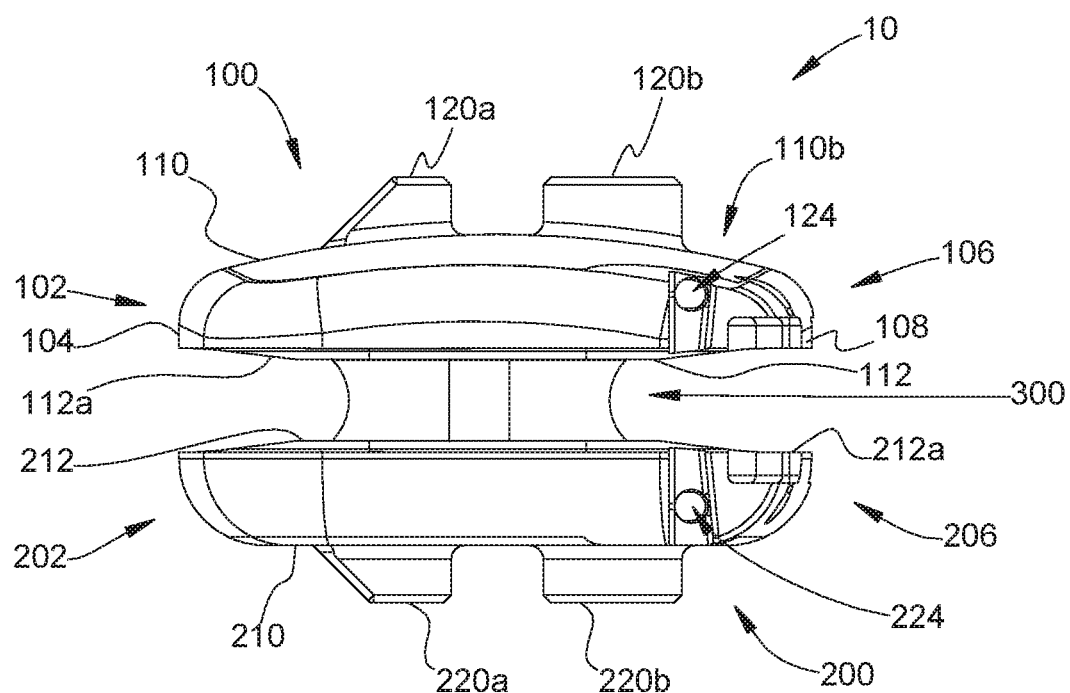
FIG. 4 is a side view of the spinal implant of FIG. 1.

As best illustrated in FIG. 4, outer surface 110 of upper end plate 100 includes a second convex profile 110b extending between first and second end surface 104, 108, although other suitable profiles are also contemplated. Second convex profile 110b includes a radius of curvature that is greater than that of first convex profile 110a (i.e., second convex profile 110b is more curvate than first convex profile 110a). In embodiments, the radius of curvature of second convex profile 110b may be between 1.5 and 2.0 inches. Additionally, it is contemplated that second convex profile 110b may include a radius that is less than that of first convex profile 110a (i.e., second convex profile 110b is less curvate than first convex profile 110a). The first and second convex profiles 110a, 110b enable the outer surface 110 of the upper end plate 100 to more closely conform to the natural concavity of the adjacent vertebral endplates. In this manner, the spinal implant 10 may be fitted to the respective vertebral implants using less cutting or shaving of the vertebral endplates and inhibits migration of the spinal implant 10 within the intervertebral space.

Although inner surface 112 is illustrated as being substantially planar, other suitable profiles are contemplated, such as concave, convex, or the like. Inner surface 112 includes a tapered edge 112a that extends around the perimeter of inner surface 112 and converges with outer surface 110 as inner surface 112 extends towards first and second end surfaces 104, 108 and opposed side surfaces 114, 116. In embodiments, tapered edge 112a defines an angle of about 7 degrees with respect to inner surface 112, although it is contemplated that tapered edge 112a may define an angle between 5 and 10 degrees with respect to inner surface 112.

Figure 3A:
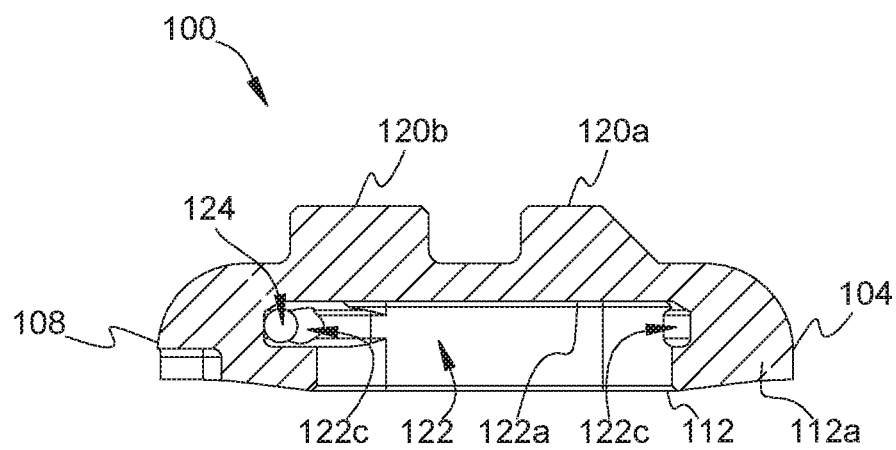
FIG. 3A is side, cross-sectional view of the an upper end plate of the spinal implant of FIG. 3, taken along line 3A-3A.
Figure 5:
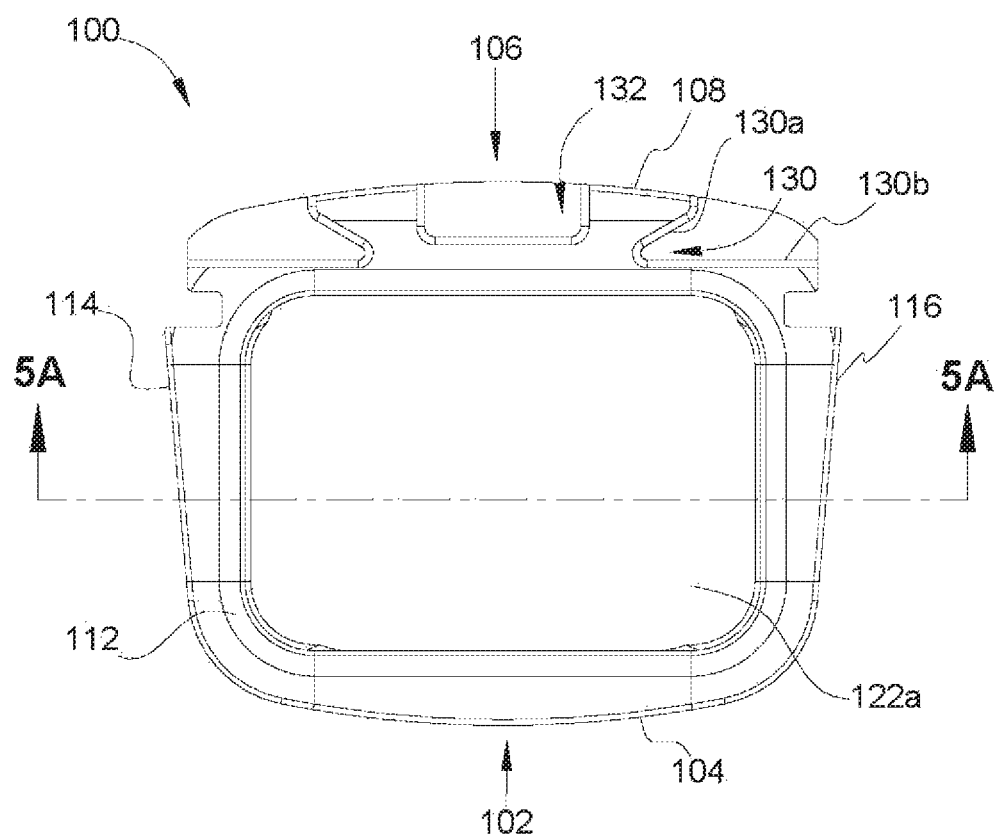
FIG. 5 is a bottom view of an upper end plate of the spinal implant of FIG. 1.
Figure 5A:
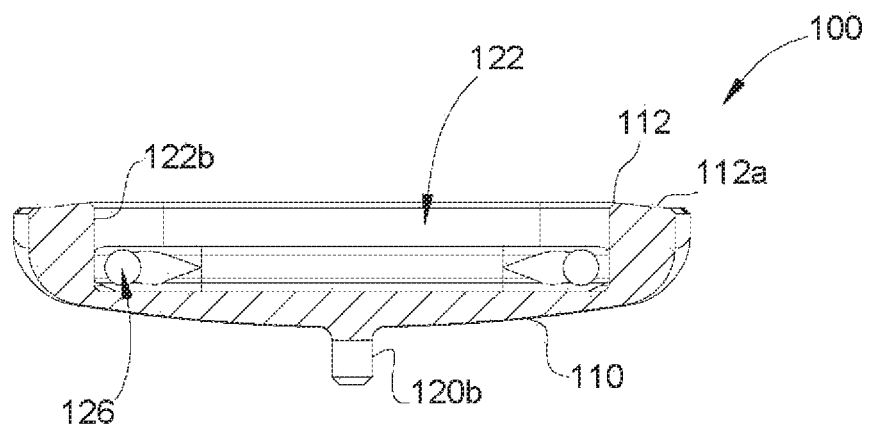
FIG. 5A is a rear, cross-sectional view of the upper end plate of FIG. 5 taken along line 5A-5A.

With reference to FIGS. 3A, 5, and 5A, upper end plate 100 includes a coupling recess 122 defined in inner surface 112. Coupling recess 122 is configured to receive core 300 (FIG. 1), as will be described in further detail hereinbelow. Although illustrated has having a profile similar to that of the outer profile of upper end plate 100, coupling recess 122 may include any suitable profile capable of receiving core 300. Coupling recess 122 includes a base surface 122a and is defined by a peripheral sidewall 122b. A retaining groove 122c is defined in peripheral sidewall 122b adjacent base surface 122a. As best illustrated in FIG. 3A, the depth of retaining groove 122c is greater adjacent second end surface 108 than first end surface 104 such that retaining pin 400 may be selectively received within retaining groove 122c adjacent second end surface 108. In this manner, when retaining pin 400 (FIG. 1) is fully advanced within retaining groove 122c, core 300 is selectively secured within coupling recess 122, as will be described in further detail hereinbelow.

Returning to FIG. 4, a lumen 124 is defined through each of opposed side surfaces 114, 116 and channel 122b such that lumen 124 is in communication with channel 122b. Lumen 124 is sized and dimensioned to accept retaining pin 400 as will be discussed in further detail hereinbelow. A pair of through-bores 126 (FIG. 3) is defined through second end surface 108 such that the pair of through-bores 126 is in communication with channel 122b. Through-bores 126 are sized and dimensioned to receive a suitable tool capable of deforming retaining pin 400, as will be described in further detail hereinbelow.

As best illustrated in FIG. 5, a pair of reliefs 130 is defined in inner surface 112 adjacent to second end surface 108. Reliefs 130 include a tapered end surface 130a that tapers toward an inner portion of upper end plate 100 in a distal direction and terminates in a planar surface 130b that extends towards each of opposed side surfaces 114, 116. Reliefs 130 are configured to selectively engage an insertion tool 600 (FIGS. 9-10A), as will be described in further detail hereinbelow. In embodiments, tapered end surface 130a forms an angle with respect to planar surface 130b of about 30 degrees, although other suitable angles are also contemplated. A locating groove 132 is defined in inner surface 112 substantially centered between the pair of reliefs 130. Locating groove 132 is configured to engage a tongue 622a of insertion tool 600 (FIGS. 9A and 10A). In this manner, when insertion tool 600 is engaged with spinal implant 10, tongue 622a is advanced into locating groove 132 to maintain the position of the upper and lower end plates 100, 200 in relation to the insertion tool 600.

Referring back to FIG. 1, lower end plate 200 provided in accordance with the present disclosure is illustrated. Lower end plate 200 is substantially similar to upper end plate 100, except that lower end plate 200 includes a substantially planar outer surface 210 and the radius of the perimeter of an outer surface 210 of lower end plate 200 may be between 0.5 and 1.00 inches. In one embodiment, the radius of the perimeter of outer surface 210 is 0.75 inches.

Upper and lower end plates 100, 200 may be constructed of any suitable biocompatible material having appropriate strength and rigidity, such as stainless steel, titanium, titanium alloy, cobalt chrome, polyetheretherketone (PEEK), or the like. In embodiments, upper and lower end plates 100, 200 are formed from an extra-low interstitial titanium alloy, Ti-6Al-4V. Additionally, it is contemplated that a titanium plasma spray coating may be applied to outer surfaces 110, 210. In embodiments, the titanium plasma spray coating may be between 0.005-0.010 inches thick, although other thicknesses are also contemplated. The average surface roughness of the plasma spray coating may be approximately 92 microinches, 128 microinches, or 134 microinches, although other average surface roughnesses are also contemplated. As can be appreciated, the surface roughness of the upper and lower end plates, 100, 200 enhances the ability of the vertebral endplates to grip the upper and lower endplates 100, 200 and enhances osteointegration of the spinal implant 10.

An embodiment of core 300 provided in accordance with the present disclosure is illustrated in FIG. 1. Core 300 is formed from a suitable biocompatible elastomeric material having appropriate strength and durometer hardness to provide sufficient axial strength to support axial spinal column loads and permit the required flexibility in motion of a spinal motion segment, such as antero-posterior bending, lateral bending, and torsion. In one embodiment, core 300 is formed from poly-carbonate-polyurethane copolymers or blends, although other elastomeric materials are also contemplated. Core 300 includes a generally barbell shaped configuration defining an upper surface 302 and an opposed lower surface 304, each defining a generally planar configuration. In plan view, core 300 includes a profile that is substantially similar to that of coupling recess 122. A flange 306 is defined on the perimeter of each of upper and lower surfaces 302, 304 that is configured to selectively engage retaining groove 122c (FIG. 3A, as will be described in further detail hereinbelow. Core 300 is coupled to each of upper and lower end plates 100, 200 to form spinal implant 10. For a detailed discussion of an exemplary core, reference can be made to commonly owned U.S. Pat. No. 8,182,534, the entire contents of which are incorporated herein by reference.

Continuing with FIG. 1, retaining pin 400 provided in accordance with the present disclosure is illustrated. Retaining pin 400 is configured to be advanced within lumens 124, 224 of upper and lower end plates 100, 200 to retain core 300 within coupling recess 122, 222 of upper and lower end plates 100, 200, respectively. Retaining pin 400 includes an elongate body having a substantially circular cross section, although other cross sections are contemplated, such as oval, square, or the like. Retaining pin 400 may be formed of any suitable biocompatible material capable of being easily deformed, but retaining enough strength to retain core 300 within each of upper and lower end plates 100, 200. In one embodiment, retaining pin 400 is formed from grade 2 commercially pure titanium, although other materials are also contemplated.

With reference to FIGS. 1-5A, a method of assembling spinal implant 10 is described. Initially, core 300 is advanced within coupling recess 122 of upper end plate 100 such that upper surface 302 of core 300 abuts base surface 122a. At this point, core 300 may be slid distally such that flange 306 engages retaining groove 122c. Next, retaining pin 400 is advanced within lumen 124 of upper end plate 100 until retaining pin 400 is fully advanced within retaining groove 122c. At this point, a suitable tool (not shown) may be advanced within each of the pair of through-bores 126 to deform retaining pin 400 around flange 306 of core 300 and secure core 300 within coupling recess 122. Lower end plate 200 is then advanced over an opposite end of core 300 such that lower surface 304 of core 300 abuts inner surface 222a of lower end plate 200. At this point, lower end plate 200 may be slid distally such that flange 306 engages retaining groove 222c. A second retaining pin 400 may then be advanced within lumen 224 of lower end plate 200 in a similar fashion to that of the first retaining pin. Once fully advanced within lumen 224, a suitable tool (not shown) may be advanced within each of the pair of through-bores 226 of lower end plate 200 to deform retaining pin 400 around flange 306 and secure core 300 within coupling recess 222 of lower end plate 200. At this point, spinal implant 10 is assembled and ready to be advanced within an intervertebral space.

Figure 7:
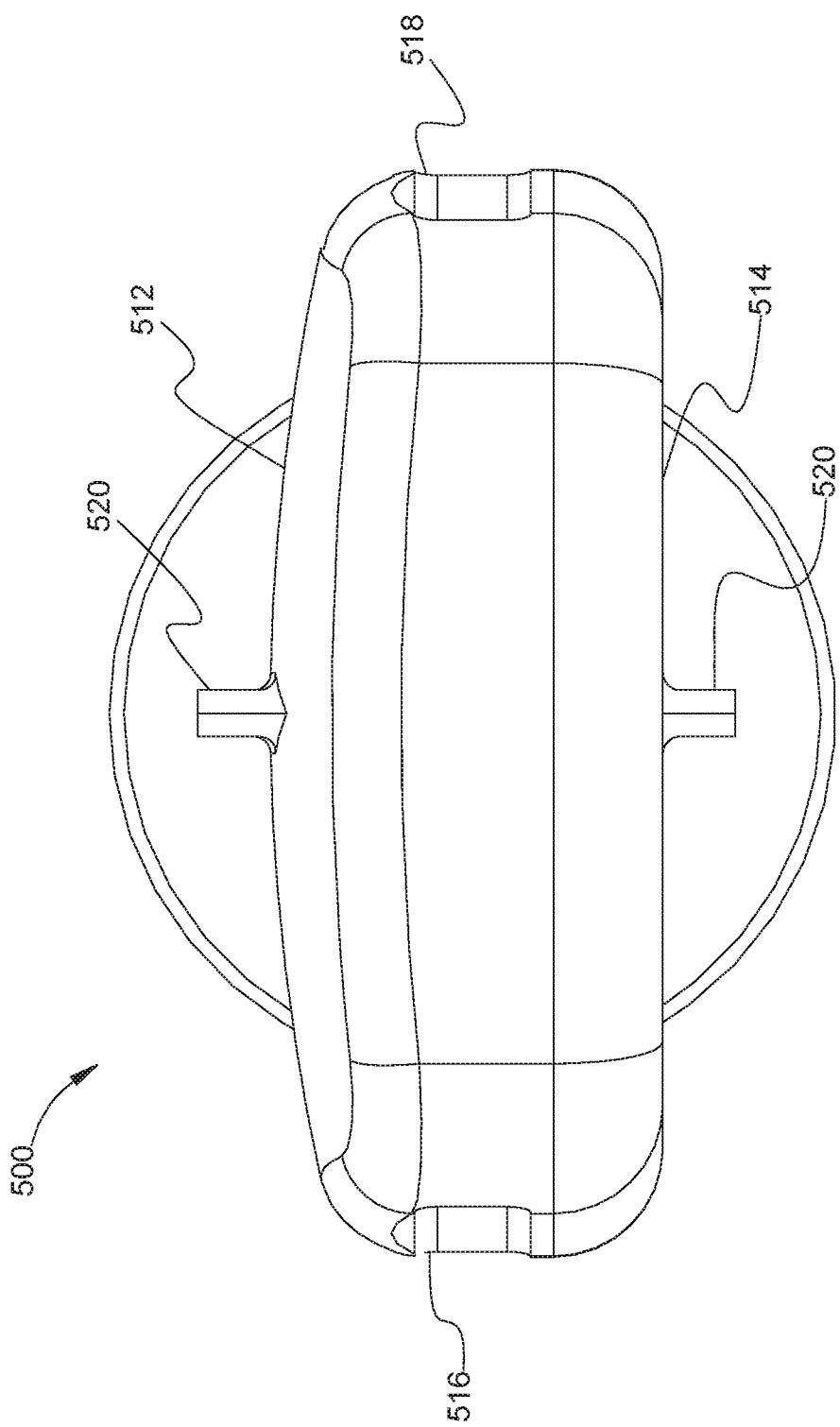
FIG. 7 is a front view of the trial inserter of FIG. 6.
Figure 8:
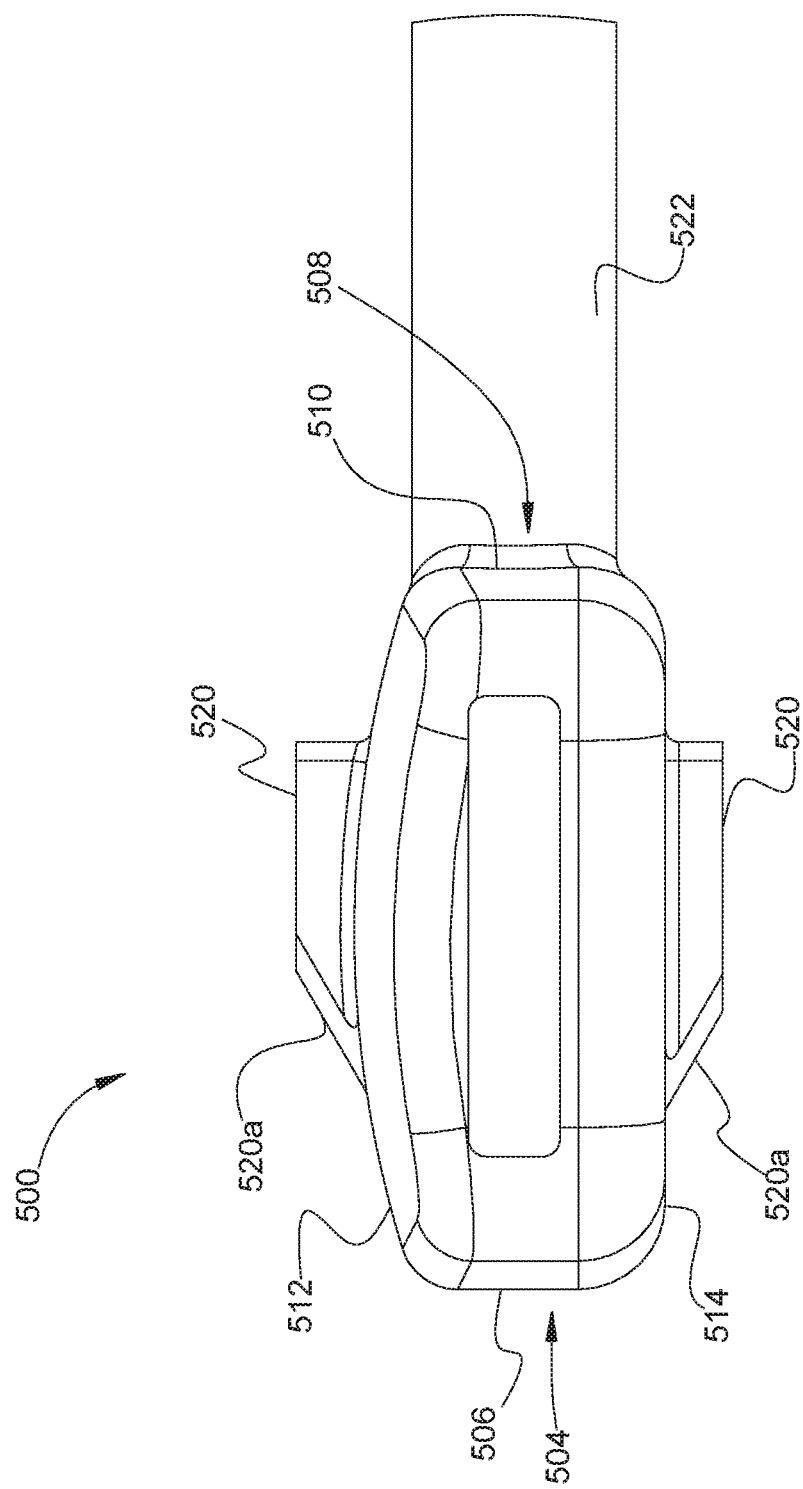
FIG. 8 is a side view of the trial inserter of FIG. 6.

Turning now to FIGS. 6-8, a trial inserter is illustrated and generally referred to as reference numeral 500. Trial inserter 500 is sized and dimensioned to replicate the overall dimensions of spinal implant 10 and is utilized to cut a slot or groove within each adjacent vertebral body (not shown) in order to permit fins 120a, 120b and 220a and 220b of upper and lower end plates 100, 200, respectively, to advance therewithin. In this manner, trial inserter 500 includes a body 502 including a substantially planar, first end surface 506 at a distal or leading end 504, and a second end surface 510, opposite thereto at a proximal or trailing end 508 (FIG. 8) having a substantially planar configuration. Body 502 extends between first and second end surfaces 506, 510 to define respective top and bottom surfaces 512 and 514 (FIG. 8), respectively, as well as opposed side surfaces 516 and 518. Top and bottom surfaces 512, 514 are illustrated as being substantially parallel to each other; however, it is contemplated that top surface 512 may be planar, convex, or the like, and top surface 512 may approximate bottom surface 514, or vice versa. Opposing side surfaces 516, 518 may form an oblique angle with respect to first end surface 506, such that body 502 increases in width in a proximal direction. Antero-posterior fins 520 are disposed centrally on top and bottom surfaces 512, 514 and extend outwardly therefrom. A leading or distal edge 520a of fins 520 is chamfered such that the height of fins 520 increases in a proximal direction. As best illustrated in FIG. 6, leading edge 520a is sharpened to include a knife profile in order to enable trial inserter 500 to cut a groove within adjacent vertebral bodies (not shown) as trial inserter 500 is advanced within the intervertebral space. An elongate handle 522 is disposed on second end surface 510 and extends proximally therefrom. Elongate handle 522 enables a clinician to grasp and maneuver trial inserter 500. It is contemplated that trial inserter 500 may be provided in various sizes to prepare the intervertebral space to accept a properly sized spinal implant 10 for each specific patient.

Figure 10:
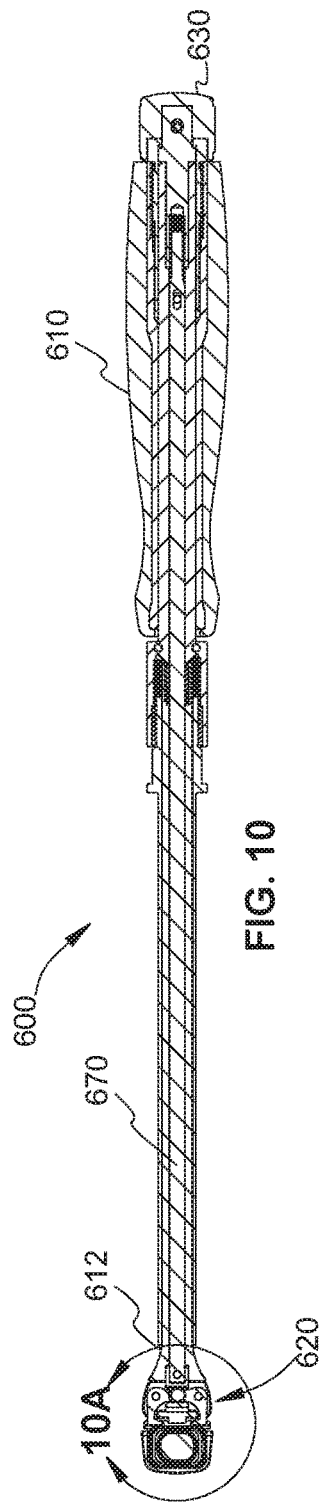
FIG. 10 is a top, cross-sectional, view of the insertion tool of FIG. 9 shown in an approximated position.
Figure 10A:
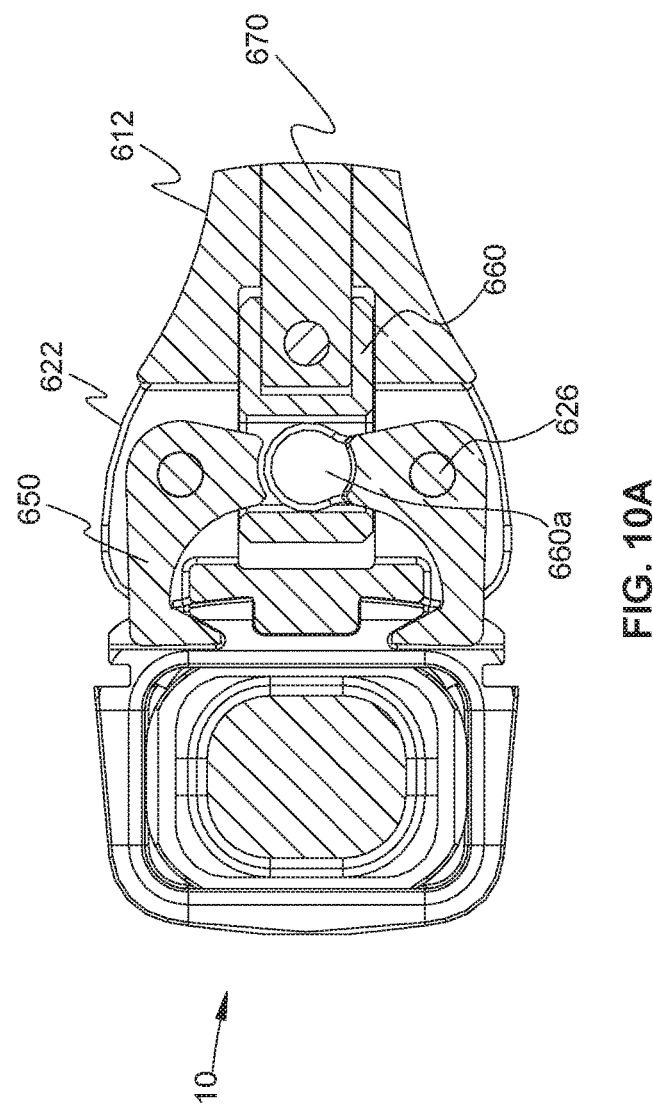
FIG. 10A is an enlarged view of the area of detail of FIG. 10.

Referring now to FIGS. 9-10A, an insertion tool 600 provided in accordance with the present disclosure is illustrated. Insertion tool 600 includes a handle portion 610 including proximal and distal ends 610a and 610b. An outer shaft 612 extends distally from the distal end 610a of handle portion 610 and terminates in end effector 620. An actuation knob 630 is rotatably disposed on proximal end 610b of handle portion 610 and is in mechanical communication with barrel nut 640. Barrel nut 640 includes a generally t-shaped profile and is rotatably secured within a proximal end of a through-hole 614 defined through proximal and distal ends 610a, 610b of handle portion 610.

End effector 620 includes a housing portion 622 disposed on a distal end of outer shaft 612. Housing portion 622 includes a cavity 624 defined therein including a pair of posts 626 disposed on an inner surface 624a thereof and a longitudinal channel 628 defined therein. A tongue 622a is disposed on a distal end 622b of housing portion 622 and extends distally therefrom. Tongue 622a is configured to be advanced into, and selectively engage, locating grooves 132, 232, of upper and lower end plates 100, 200 respectively. A pair of opposed jaw members 650 is rotatably disposed on a respective one of the pair of posts 626 such that opposed jaw members 650 are capable of rotating from a first, open position (FIG. 9A), to a second, approximated position (FIG. 10A). Each of the opposed jaw members 650 includes a generally C-shaped profile, a distal end 650a of each of which includes a protrusion 650b configured to selectively engage a respective one of the pair of reliefs 130, 230 of upper and lower end plates 100, 200, respectively. A proximal end 652 of opposed jaw members 650 is rotatably secured to a shuttle 660 slidably disposed within channel 628. Each of opposed jaw members 650 are rotatably disposed about a shuttle pin 660a disposed on shuttle 600. An inner shaft 670 is slidably disposed within a lumen 612a defined through outer shaft 612. A distal end 670a of inner shaft is coupled to shuttle 660 and a proximal end 670b is threadedly engaged with barrel nut 640. In this manner, when actuation knob 630 is rotated in a first direction, barrel nut 640 is caused to be rotated, thereby drawing inner shaft 670 in a proximal direction. As inner shaft 670 is drawn in a proximal direction, shuttle 660 is likewise drawn in a proximal direction, thereby causing the pair of opposed jaw members 650 to rotate about their respective posts 626 and shuttle pin 660a to actuate the opposed jaw members 650 from the first, open position (FIG. 9A), to the second, approximated position (FIG. 10A). Rotating actuation knob 630 in an opposite, second direction, reverses the operation of insertion tool 600, thereby causing the opposed jaw members 650 to move from the second, approximated position, to the first, open position to release spinal implant 10 from insertion tool 600.

Figure 12A:
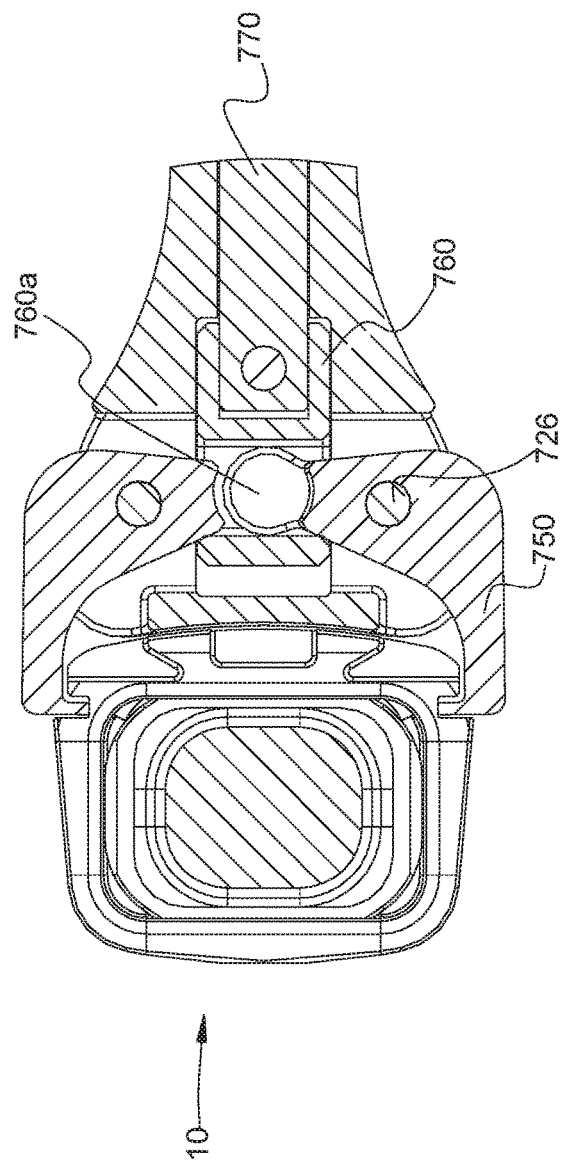
FIG. 12A is an enlarged view of the area of detail of FIG. 12.

With reference to FIGS. 11-12A, a removal tool 700 provided in accordance with the present disclosure is illustrated. Removal tool 700 is substantially similar to insertion tool 600, and therefore, in the interest of brevity, only the differences therebetween will be described hereinbelow. Opposed jaw members 700 are configured to grasp the notches 118, 218 of upper and lower end plates 100, 200, respectively. In this manner, opposed jaw members 700 are spaced apart a greater amount when in a first, open position in order to facilitate grasping the widely spaced pair of notches 118, 218. Additionally, the distal end 722b of housing portion 722 includes a generally blunt configuration, and does not include a tongue feature. As such, distal end 722b of housing portion 722 abuts second end surfaces 108, 208 of upper and lower end plates 100, 200, respectively. These structural differences enable a clinician to more quickly and easily remove spinal implant 10 from the intervertebral space.

With reference again to FIGS. 9-10A, a method of inserting spinal implant 10 into the intervertebral space between adjacent vertebral bodies during the course of a spinal surgical procedure is described. Initially, an appropriately sized upper and lower end plate 100, 200 is selected. This may be determined by using an appropriately sized trial inserter to gauge the thickness and width of spinal implant 10 to utilize, as will be described in further detail hereinbelow. Thereafter, spinal implant 10 is assembled in the manner described hereinabove. Once spinal implant 10 is fully assembled, the intervertebral space (not shown) is prepared, e.g., damaged or diseased tissue is removed. At this point, each adjacent vertebral body may be temporarily spread apart using a vertebral jack tool or other suitable device. Thereafter, trial inserter 500 is advanced within the intervertebral space. As trial inserter 500 is advanced within the intervertebral space, the leading edge 520a of fins 520 cut a groove (not shown) in each of the adjacent vertebral bodies. Next, trial inserter 500 is removed from the intervertebral space. The process of inserting and removing a trial inserter 500 from the intervertebral space may be repeated in order to determine the appropriately sized spinal implant. At this point, insertion tool 600 is secured to spinal implant 10 by first aligning tongue 622a with each locating groove 132, 232 of upper and lower end plates 100, 200, and thereafter, rotating actuation knob 630 in a first direction to cause opposed jaw members 650 to rotate from the first, open position, to the second, approximated position and grasp the pair of reliefs 132, 232 of upper and lower endplates 100, 200. Next, spinal implant 10 is advanced within the intervertebral space such that fins 120a, 120b and 220a, 220b of upper and lower end plates 100, 200 respectively, align with the groove (not shown) cut in each of the adjacent vertebral bodies by trial inserter 500. Once spinal implant 10 is positioned in the desired location, actuation knob 630 is rotated in a second direction to cause opposed jaw members 650 to rotate from the second, approximated position, to the first, open position and release spinal implant 10.

Referring now to FIGS. 11-12A, a method of removing spinal implant 10 from the intervertebral space between adjacent vertebral bodies during the course of a spinal surgical procedure is described. Initially, if required, a vertebral jack tool or other suitable surgical device may be inserted between each adjacent vertebral body in order to jack open the vertebral space. Thereafter, removal tool 700 is advanced within the intervertebral space until the distal end 722b of housing portion 722 abuts second end surfaces 108, 208 of upper and lower end plates 100, 200, respectively. At this point, actuation knob 730 is rotated in a first direction to cause opposed jaw members 750 to rotate from the first, open position (FIG. 11A), to the second, approximated position (FIG. 12A) and grasp the pair notches 118, 218 of upper and lower end plates 100, 200, respectively. Thereafter, spinal implant 10 is pulled in a proximal direction using removal tool 700 and removed from the intervertebral space. At this point, actuation knob 730 is rotated in a second direction to cause opposed jaw members 750 to rotate from the second, approximated position, to the first, open position, and release spinal implant 10 from the removal tool 700. It is also contemplated that the procedure described above may be reversed in order to insert or reposition spinal implant 10.

It is also contemplated that spinal implant 10 may be provided in the form of a kit, including upper and lower end plates 100, 200, core 300, and retaining pins 400. It is contemplated that each of upper and lower end plates 100, 200 may be provided in various sizes in order to accommodate a variety of patients. It is further contemplated that the kit may include insertion tool 600 and removal tool 700. In this manner, the clinician may select upper and lower end plates 100, 200 having various sizes and/or convex profiles to most accurately match the patient's anatomy, select various cores 300 having various stiffnesses, elasticities, or the like, may select an upper end plate 100 that is of a different size than a lower end plate 200, or vice versa, or any other suitable combination.

It will be understood that various modifications may be made to the embodiments of the presently disclosed spinal implant. Therefore, the above description should not be construed as limiting, but merely as exemplifications of embodiments. Those skilled in the art will envision other modifications within the scope and spirit of the present disclosure.

What is claimed is:

1. A spinal implant, comprising:
   an upper end plate including an outer surface extending between first and second end surfaces and opposed side surfaces, wherein the outer surface includes a first convex profile extending between the first and second end surfaces and a second convex profile extending between the opposed side surfaces, the first convex profile and the second convex profile having different curvatures, the upper end plate also including a first lumen extending through one of the opposed side surfaces thereof;
   first and second retaining pins;
   a lower end plate including opposed side surfaces and a second lumen extending through one of the opposed side surfaces thereof; and
   a core disposed between the upper and lower end plates and coupled thereto, respectively, via the first and second retaining pins being advanced into the first and second lumens,
   wherein the first and second retaining pins remain undeformed when the first and second retaining pins are fully advanced into the respective first and second lumens, and are deformable upon engagement with a tool adapted to deform the retaining pins after the retaining pins have been fully advanced into the respective first and second lumens.

2. The spinal implant of claim 1, wherein the lower end plate includes an outer surface extending between first and second end surfaces and opposed side surfaces.

3. The spinal implant of claim 2, further including a pair of antero-posterior fins disposed on each of the outer surfaces of the upper and lower end plates, wherein the pairs of antero-posterior fins extend outwardly from the respective outer surfaces.

4. The spinal implant of claim 3, wherein each pair of antero-posterior fins includes an anterior fin and a posterior fin, wherein the anterior fin and posterior fin are spatially arranged such that a gap exists therebetween.

5. The spinal implant of claim 4, wherein a leading edge of each posterior fin is chamfered such that the height of the posterior fin increases in an anterior direction.

6. The spinal implant of claim 2, wherein each of the upper and lower end plates includes a trapezoidal profile in a plan view.

7. The spinal implant according to claim 1, wherein a proximal end of each of the upper and lower end plates includes a pair of reliefs configured to releasably engage an insertion tool.

8. The spinal implant according to claim 7, wherein a proximal end of each of the upper and lower end plates further includes a pair of notches configured to releasably engage a removal tool.

9. The spinal implant according to claim 1, wherein the upper end plate includes an inner base surface and a peripheral sidewall adjacent the inner base surface, the inner base surface and peripheral wall defining a coupling recess, the core being disposed within the coupling recess of the upper end plate.

10. The spinal implant according to claim 9, wherein:
    the coupling recess includes a retaining groove extending into the peripheral sidewall,
    the core includes a flange, the flange engaging the retaining groove, and
    the first retaining pin being disposed within the retaining groove to engage the core and secure it to the upper end plate.

11. The spinal implant according to claim 10, wherein the first retaining pin has a first configuration when fully advanced into the first lumen in which the retaining pin is undeformed and a second configuration in which the retaining pin is deformed via a tool from the first configuration about a portion of the core.

12. A spinal implant, comprising:
    first and second end plates each including an outer bone contact surface, an inner base surface, and a peripheral sidewall adjacent the base surface, the inner base surface and peripheral sidewall defining a coupling recess, the peripheral sidewall defining a lumen extending therethrough and intersecting the coupling recess;
    a core disposed within the coupling recesses of the first and second end plates; and
    a pair of retaining pins each disposed in a fully advanced position within the lumen and coupling recess of the respective first and second end plates to secure the core to the upper and lower end plates, the retaining pins being in an undeformed configuration when in the fully advanced position, and deformable upon engagement with a tool adapted to deform the retaining pins while in the fully advanced position.

13. The spinal implant according to claim 12, wherein the core is formed from an elastomeric material.

14. The spinal implant according to claim 12, wherein the outer bone contact surface of each of the first and second end plates extends between first and second end surfaces and opposed side surfaces, wherein the outer bone contact surface includes a first convex profile extending between the first and second end surfaces and defining a first radius of curvature and a second convex profile extending between the opposed side surfaces and defining a second radius of curvature, the first radius of curvature being different than the second radius of curvature.

15. The spinal implant according to claim 12, wherein the coupling recess of each of the first and second end plates includes a retaining groove extending into the peripheral sidewall, and a portion of the core is disposed within the retaining grooves of the first and second end plates.

16. The spinal implant according to claim 15, wherein the retaining pins are each disposed within the retaining groove of their respective end plate.

17. A spinal implant, comprising:
an upper end plate and a lower end plate each including an outer bone contact surface extending between first and second end surfaces and opposed side surfaces, the first and second end surfaces and opposed side surfaces each partially defining a peripheral sidewall extending about a perimeter of each of the upper and lower end plates, the upper and lower end plates each having a retaining groove and a lumen extending through the peripheral sidewall and into the retaining groove;
a core disposed between the upper and lower end plates and engaging the retaining groove of each of the upper and lower end plates; and
retaining pins respectively disposed within the lumens of the upper and lower end plates and engaging the core so as to secure the core to the first and second end plates,
wherein the retaining pins have an underformed configuration and a deformed configuration, the retaining pins remaining in the undeformed configuration when fully advanced within their respective lumens, and transforming to the second configuration upon engagement with a tool adapted to deform the retaining pins while in the fully advanced position within the lumens.

18. The spinal implant according to claim 17, wherein the upper and lower end plates each include a pair of bore holes communicating with the retaining groove and being configured to receive the tool.

19. The spinal implant according to claim 17, wherein the outer bone contact surface of each of the upper and lower end plates includes a first convex profile extending between the first and second end surfaces and defining a first radius of curvature and a second convex profile extending between the opposed side surfaces and defining a second radius of curvature, the first radius of curvature being different than the second radius of curvature.

* * * * *